US00PP09626P

United States Patent [19]

Egger

[11] Patent Number: Plant 9,626

[45] Date of Patent: Aug. 13, 1996

[54] LONGIFLORUM×ASIATIC HYBRID LILY PLANT 'CEB DAZZLE'

[76] Inventor: Donald L. Egger, 7115 SW. Frog Pond La., Wilsonville, Oreg. 97070

[21] Appl. No.: 447,934

[22] Filed: May 23, 1995

[51] Int. Cl.[6] ..... A01H 5/00

[52] U.S. Cl. ..... Plt./87.4

[58] Field of Search ..... Plt./87.4

[56] References Cited

U.S. PATENT DOCUMENTS

P.P. 9,245 8/1995 Egger ..... Plt./87.4

P.P. 9,249 8/1995 Egger ..... Plt./87.4

*Primary Examiner*—James R. Feyrer

[57] ABSTRACT

A new and distinct lily hybrid named 'Ceb Dazzle' characterized by upright, large yellow colored flowers with thick petals on tall, strong stems excellent for cut flower production.

1 Drawing Sheet

BACKGROUND OF THE INVENTION

The present invention comprises a new and distinct cultivar of Lily hybrid, referred to commercially as a Longiflorum-Asiatic Lily Hybrid, referred to by the cultivar name 'Ceb Dazzle'.

This invention is the product of a controlled breeding program in Aurora, Oreg. The seed parent was an unnamed seedling identified as GH-403. This seed parent has not been released and was kept proprietary. The pollen parent was AM #2, another proprietary non-released plant.

The Longiflorum-Asiatic cross is relatively new to the trade. This type of cross was originally made to create colored *Lilium longiflorum* hybrids. Instead, due to the difficulty in crossing back to *L. longiflorum,* the plants that were developed had to be crossed with Asiatic lilies. As such, the results look more like Asiatic lilies. The resulting hybrids often have several advantages over an Asiatic lilly: (1) often larger flowers; (2) often larger, waxier leaves; (3) hybrid vigor; (4) lower susceptibility to scorch; (5) excellent flower texture and substance; (6) more virus resistance; (7) new and clearer colors; and (8) stronger, sturdier stems.

This invention has not been observed under all possible environmental conditions, The phenotype may vary significantly with variations in environment such as temperature, light intensity, and day length, without, however, any variation in genotpe. The following traits have been repeatedly observed in asexually propagated progeny and are determined to be the basic characteristics of this invention which in combination distinguish this lily as a new and distinct cultivar: (1) large, upright, bright yellow flowers with a lighter blush and some maroon spots; (2) large, yellow buds; (3) thick tepals with wavy outer tepal margins; (4) tall, strong stems for cut flowers; and (5) excellent vase life. Bulbs of this plant may be precooled and forced out of season for very uniform cut flower production.

To the inventor's knowledge, the only other Longiflorum-Asiaatic lily hybrids that are somewhat similar to the varieties 'Geb Glow', allowed U.S. Patent Application Ser. No. 08/333,257, filed Nov. 2, 1994, now U.S. Plant Pat. No. 9,245 and 'Ceb Sun', allowed U.S. Patent Application Ser. No. 08/333,495, filed Nov. 2, 1994 now U.S. Plant Pat. No. 9,249. Compared to 'Ceb Glow', 'Ceb Dazzle' has taller stems, larger leaves and flowers, and broader tepals. Compared to 'Ceb Sun', 'Ceb Dazzle' has larger leaves, slightly smaller and lighter colored flowers, and wavy outer tepal margins Asexual reproduction of this new variety has been initially and subsequently accomplished at Cebeco Lilies, Inc. in Aurora, Oreg., by scaling and tissue culture. The resulting plants have shown that the above-mentioned unique features are stable and reproduce true to type in each successive propagation.

Figure 2:
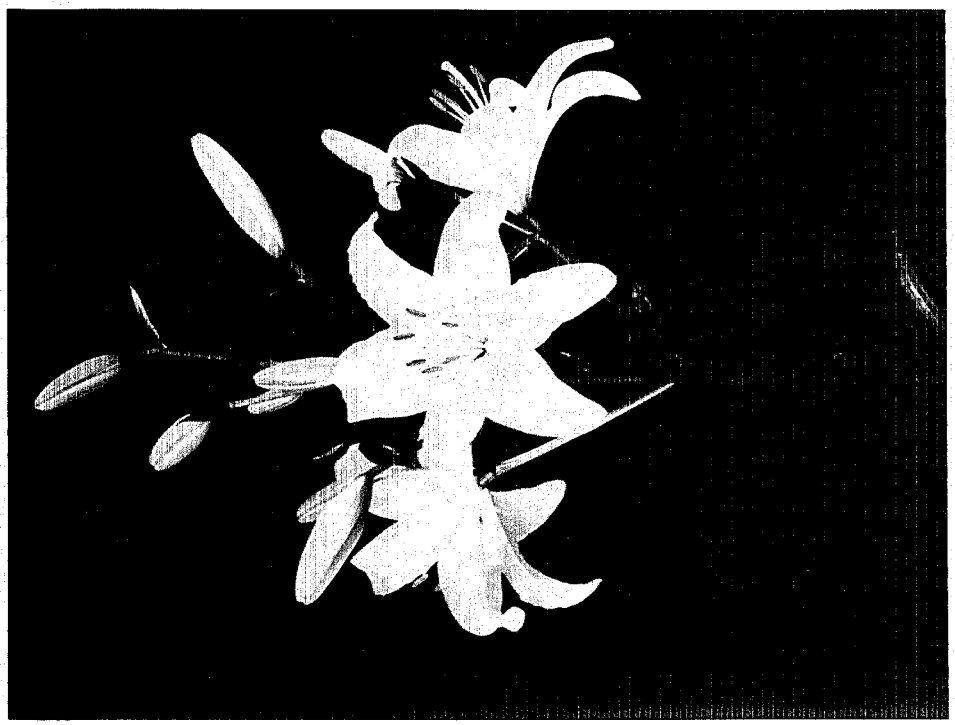
FIG. 2 is a photograph showing the 'Ceb Dazzle' lily.
Figure 1:
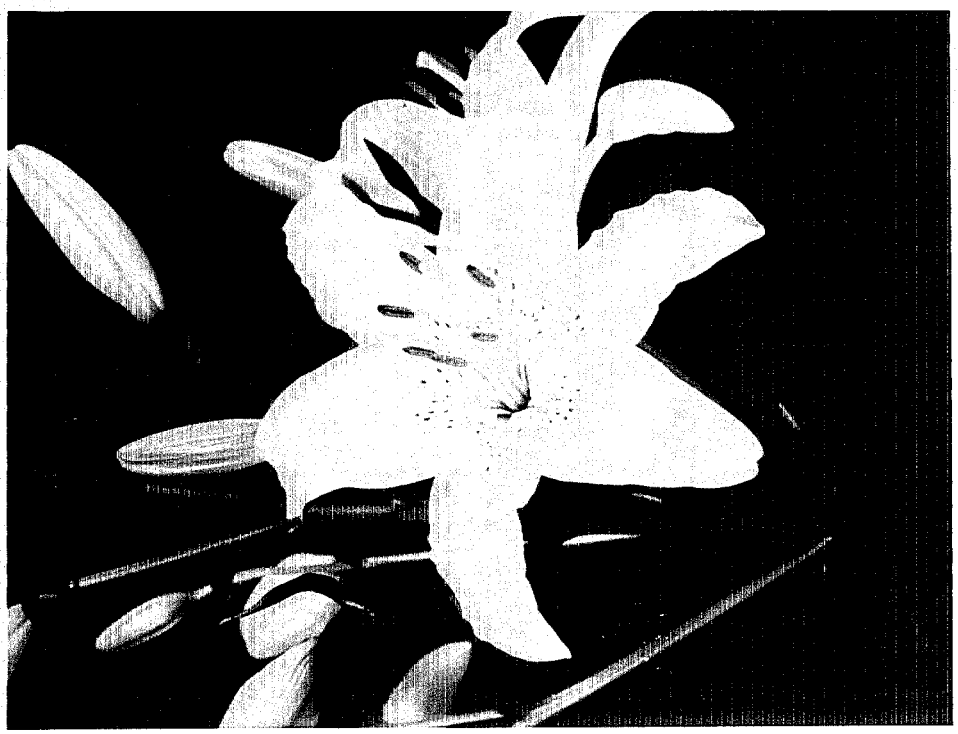
FIG. 1 is a close-up photograph which illustrates in great detail a single flower of the new plant.

The photographs of the drawing were taken in August 1993 in a studio and illustrate the tpical flower and foliage form, with color being as true as is reasonably possible in this ttpe of color photograph.

DETAILED DESCRIPTION

The following is a detailed description of the invention based on plants produced under commercial practices in the Cebeco Lilies, Inc. greenhouses in Aurora, Oreg. in July 1993. Color references are made to The Royal Horticultural Society Colour Chart (R.H.S.), except where the context indicates a term having its ordinary dictionary meaning.

THE PLANT

Origin: Seedling.

Parentage:

*Seed parent.*—GH-403.

*Pollen parent.*—AM #2.

Commercial classification: Up Facing Longiflorum-Asiatic Hybrid, cut flower type.

Classification: Division VIII, According to the Horticultural Classification of Lilies by The Royal Horticultural Society of London.

Form: Single erect stem bearing terminal cluster of flowers.

Height: About 110 cm. from the top of the soil to the top of the flowers from bulbs of 12–14 cm. in circumference.

Growth habit: Vigorous, upright and rigid.

Foliage:

*Arrangement.*—Spiral.

*Quantity.*—Less than average, with internodes of 1.2–2 cm. long.
*Leaf size.*—Large. To about 18 cm. long and about 3.5 cm. wide.
*Leaf shape.*—Lanceolate.
*Texture.*—Leathery.
*Aspect.*—Glossy.
*Color.*—Medium green on both sides, closest to 147A.

Bulbs:
*Size.*—Variable, ranging to about 12–14 cm. in circumference as used commercially.
*Color.*—White.

THE BUD

Size: Large. To about 11.5 cm. long and 3.5 cm. wide just prior to opening.
Shape Ovoid. The bud is at a slight tilt until mature.
Rate of opening: The mature bud opens slowly in response to light.
Color: Yellow. Yellow Group 12B.

THE FLOWER

Blooming habit: Annually, once and early season.
Days to bloom: Flowers approximately 76 days after spring greenhouse planting under typical commercial flower forcing conditions of 15° Celsius night time temperatures.
Inflorescence size: About 20 cm high and 34 cm. wide when there are five flowers present.
Flower size: Large.
*Diameter.*—About 21 cm.
*Depth.*—About 4–6 cm.
Borne: In an umbel or modified raceme of 5 to 10 flowers from bulbs, 12–14 cm. in circumference.
Shape: When the flower first opens it is bowl-shaped. Later, the shape flattens out and the tepals reflex slightly at the tips.
Tepalage:
*Number.*—Six.
*Arrangement.*—Imbricated.
*Shape.*—Ovate.
*Margins.*—Slightly undulating on outer tepals.
*Texture.*—Spongy, thick.
*Aspect.*—Satiny.
Size:
*Length.*—About 12.5 cm.
*Width.*—Inner tepals —about 6 cm. Outer tepals —about 4.5 cm.
*Depth of imbrication.*—About 17 mm.
Nectary: About 3.5 cm. long; yellow green; pubescent. Channels together.
Projections: Few, inconspicuous, papillose.
Spots: About 5–20 per tepal; raised; long oval in shape; located above and around the nectary and on the adjacent margin; maroon (Grayed-Purple Group 187A).
Blush: Light Yellow, Yellow Group 9D; located around the nectary.
Color:
*Topside.*—Yellow. Yellow Group 12A-9A. Lightening to Yellow Group 9C with age.
*Topside base.*—Light Yellow. Yellow Group 9D.
*Bottomside.*—Yellow, Yellow Group 9A on edges. The centers of the outer tepals are light yellow, Yellow Group 11C. The tepal bases are the lightest yellow, Yellow Group 8D.
*Discoloration.*—Slightly lighter color
*Fragrance.*—Slight.
*Quality.*—Excellent.
Pedicel:
*Length.*—Varies from about 6–19 cm.
*Color.*—Yellow green lightly mottled with red purple.
*Orientation.*—Ascending upwardly from about 40° from the horizontal.

THE REPRODUCTIVE ORGANS

Stamens:
*Number.*—Six, typical of the genus Lilium.
*Anthers before dehiscence.*—Size: About 2.3 cm. Color: Light brown. Grayed-Orange group 177B.
*Filaments.*—Length: About 85 mm. Color: Greenish yellow. Green-Yellow Group 1A at tip lightening to Yellow Group 4D at base.
*Pollen.*—Color: Orange brown. Grayed-Orange Group 172C.
Pistil:
*Number.*—One.
*Style.*—Length: About 75 mm. Color: Yellow at top, Yellow Group 2B. Green-Yellow 1D at base.
*Stigma.*—Color: Yellow. Yellow Group 4B.

THE FRUIT

Fertility: Low.
Shape: Ovoid.
Color at Maturity: Soft brown.

I claim:

1. A new and distinct cultivar of Longiflorum-Asiatic hybrid lily plant characterized by large, upright, bright yellow flowers with a lighter blush and some maroon spots, large yellow buds, thick tepals with wavy outer tepal margins, tall, strong stems and excellent vase life.

* * * * *